US006984725B2

(12) United States Patent
Carter et al.

(10) Patent No.: US 6,984,725 B2
(45) Date of Patent: Jan. 10, 2006

(54) METHOD FOR THE SEPARATION OF TRIGLYCOALKALOIDS

(75) Inventors: Stephen John Carter, Woodvale (AU); Paul Edward Murray, Nedlands (AU); John Edward Parkin, Roleystone (AU); Gautam Dalwadi, Perth (AU)

(73) Assignee: Solbec Pharmaceuticals Ltd., Nedlands (AU)

( * ) Notice: Subject to any disclaimer, the term of this patent is extended or adjusted under 35 U.S.C. 154(b) by 97 days.

(21) Appl. No.: 10/461,737

(22) Filed: Jun. 13, 2003

(65) Prior Publication Data
US 2004/0030109 A1    Feb. 12, 2004

Related U.S. Application Data

(60) Provisional application No. 60/392,417, filed on Jun. 28, 2002.

(51) Int. Cl.
C07H 15/24    (2006.01)
C07H 1/08     (2006.01)
(52) U.S. Cl. .............................. 536/5; 536/128; 514/26
(58) Field of Classification Search .................. 514/26; 536/5, 128
See application file for complete search history.

(56) References Cited

U.S. PATENT DOCUMENTS

| 5,095,109 A | * | 3/1992 | Kuehne ....................... 540/479 |
| 5,958,770 A | | 9/1999 | Cham et al. |
| 6,214,803 B1 | | 4/2001 | Kuo et al. |

FOREIGN PATENT DOCUMENTS

| EP | 20029 | 12/1980 |
| EP | 0020029 A1 | 12/1980 |
| GB | 1108656 | 4/1968 |
| GB | 1284044 | 8/1978 |
| SU | 124450 | 12/1959 |
| WO | WO00/61153 | 10/2000 |
| WO | WO 0329269 | 4/2003 |

OTHER PUBLICATIONS

Ahmad, K. M. "Constituents of the aerial part and roots of some *Solanum melongena* varieties" Egyptian J. Pharm. Sci. (1996) vol. 37, No. 1-6, pp 37-44.*
STN File CA, Abstract 54:7652, & A.F. Bashmurin, Byull. Nauch-Tekh. Inform. Leningrad. Nauch-Issledovatel. Vet. Instit. (1958), No. 5), 34-5, Referat. Zhur. Khim., Biol. Khim 1959, Abstr. No 12166, abstract only.
STN File CA, Abstract 132:134842, & V.A. Maritza et al., Afinidad (1999), 56 (484), 393-396, abstract only.
"A new procedure for the mass extraction and collection of potato glycoalkaloids." Achterberg, C.L.et al., E.S. Dep. Food Sci., Univ. Maine, Orono, ME, USA. American POtato Journal (1979) 56(3), 145-8, abstract only.

"Method for the isolation of solasodine from fresh *Solanum laciniatum* herbs." Panina V.V. et al. Khim.-Farm Inst. Im. Ordzhonikidze, Moscow, USSR (1977), 11(2), 99-103, abstract only.
"Use of ion exchangers for separating *Solanum lacianatum* glycoalkaloids." Andreeva, L.G. et al. Khim.-Farm Inst. Im. Ordzhonikidze, Moscow, USSR. Khimiko-Farmatsevticheskii Zhurnal (1969), 3(11), 42-6, abstract only.
"Separation of steroid glycoalkaloids from plant extract." Szlavik, Laszlo et al. Herba Hungarica (1966), 5 (2-3), 218-24, abstract only.
"Determination of potato glycoalkaloids and their aglycone in blood serum by high-performance liquid chromatography. Application to pharmacokinetic studies in humans." Hellenas K E; Husbandry, Swedish University of Agricultural Sciences, Uppsala Journal of Chromotography (Jan. 3, 1992), 513, 69-78, abstract only.
"*Solanum alkaloids*. VIII. Solamargine, a new alkaloids form *Solanum marginatum*." Briggs, Lindsay H. et al., Auckland Univ. Coll., N.Z. J. Soc. Chem (1952), 3587-91, abstract only.
"Chromatographic procedures for the isolation of plant steroids" Journal of Chromatography A. vol. 935, Issues 1-2, Nov. 23, 2001, pp. 105-123, abstract only.

(Continued)

*Primary Examiner*—Leigh C. Maier
(74) *Attorney, Agent, or Firm*—Merchant & Gould P.C.

(57) ABSTRACT

In accordance with the present invention there is provided a method for the separation of a triglycoalkaloid in which the triglycoside portion comprises α-L-rhamnopyranosyl-(1→2gal)-O-β-D-glucopyranosyl-(1→3gal)-β-D-galactopyranose (or 6-deoxy-α-L-mannopyranosyl-(1→2)-O-[β-D-glucopyranosyl-(1→3)]-β-D-galactopyranoside) ('an rhamnose-glucose-galactose triglycoalkaloid') from a triglycoalkaloid in which the triglycoside portion is α-L-rhamnopyranosyl-(1→2glu)-O-α-L-rhamnopyranosyl-(1→4glu)-β-D-glucopyranose ('a rhamnose-rhamnose-glucose triglycoalkaloid') in a mixture containing both, the method comprising the steps of:

Combining the mixture with a portion of alcoholic solvent;

Causing or allowing a substantial portion of the rhamnose-rhamnose-glucose triglycoalkaloid to dissolve, thereby generating an alcoholic solution substantially of the rhamnose-rhamnose-glucose triglycoalkaloid, and a solid substantially comprising the rhamnose-glucose-galactose triglycoalkaloid; and Separating the solid substantially comprising the rhamnose-glucose-galactose triglycoalkaloid from the solution substantially of the rhamnose-rhamnose-glucose triglycoalkaloid.

30 Claims, No Drawings

OTHER PUBLICATIONS

"Isolation of solasodine and other steroidal alkaloids and sapogenins by direct hydrolysis-extraction of Saoanum plants or glycosides therefrom" Phytochemistry, vol. 58, Issue 3, Oct. 2001, pp. 501-508, abstract only.

"Isolation of steroidal glycoalkaloids from *Solanum incanum* by two countercurrent chromatographic methods" Phytochemistry, vol. 30, Issue 2, Jan. 2, 1991, pp. 685-687, abstract only.

"Partial preparative purification of leptine I from foliage of the wild potato, *Solanum chacoense* (Bitt.)." Kowalski et al. Preparative Biochemistry and Biotechnology, 30 (2) pp. 133-144, 2000, abstract only.

"Partial preparative purification of leptine I from foliage of the wild potato, *Solanum chacoense* (Bitt.)." Kowalski et al. Preparative Biochemistry and Biotechnology, 30 (2) pp. 133-144, May 2000, abstract only.

"Preparative isolation of *Solanum tuberosum* L. glycalkaloids by MPLC." Soule, S. et al. Potato Research, 40 (413-416), 1997, abstract only.

"Production of solamargine by in vitro cultures of *Solanum paludosum*." El Badaoui, H. et al., Plant Cell, Tissue and Organ Culture, 45 (2) pp. 123-127, 1996, abstract only.

* cited by examiner

METHOD FOR THE SEPARATION OF TRIGLYCOALKALOIDS

RELATED APPLICATIONS

This application claims priority to provisional application Ser. No. 60/392,417, filed 28 Jun. 2002, entitled "METHOD FOR THE SEPARATION OF SOLAMARGINE AND SOLASONINE", which is specifically incorporated by reference herein.

FIELD OF THE INVENTION

The present invention relates to a method for the separation of triglycoalkaloids. More specifically, the present invention relates to a method for the separation of triglycoalkaloids in which the triglycoside portion comprises α-L-rhamnopyranosyl-( 1→2gal)-Oβ-D-glucopyranosyl-(1→3gal)-β-D-galactopyranose (or 6-deoxy-α-L-mannopyranosyl-( 1→2)-O-[β-D-glucopyraonosyl-(1→3)]-β-D-galactopyranoside) and triglycoalkaloids in which the triglycoside portion is α-L-rhamnopyranosyl-( 1→2glu)-O-α-L-rhamnopyranosyl-(1→4glu)-β-D-glucopyranose from a mixture containing both compounds.

BACKGROUND ART

Glycoalkaloids in which the triglycoside portion comprises α-L-rhamnopyranosyl-( 1→2gal)-O-β-D-glucopyranosyl-(1→3gal)-β-D-galactopyranose (or 6-deoxy-α-L-mannopyranosyl-( 1→2)-O-[β-D-glucopyranosyl-(1→3)]-β-D-galactopyranoside) occur together with triglycoalkaloids in which the triglycoside portion is α-L-rhamnopyranosyl-( 1→2glu)-O-α-L-rhamnopyranosyl-(1→4glu)-β-D-glucopyranose in plant extracts. For example, solasonine and solamargine, which occur together in the same plant extracts, are triglycoalkaloids in which the alkaloid portion is common, being solasadine, but the triglycoside portion differs. The triglycoside portion of solasonine is α-L-rhamnopyranosyl-(1→2gal)-O-β-D-glucopyranosyl-( 1→3gal)-β-D-galactopyranose (or 6-deoxy-α-L-mannopyranosyl-(1→2)-O-[β-D-glucopyraonosyl-( 1→13)]-β-D-galactopyranoside), whilst the triglycoside portion of solamargine is α-L-rhamnopyranosyl-(1→2glu)-O-α-L-rhamnopyranosyl-(1→4glu)-β-D-glucopyranose.

Similarly, the triglycoalkaloids α-solanine and α-chaconine occur together in plant extracts. These compounds share a common alkaloid portion, being solanidine, but, again, the triglycoside portion differs. The triglycoside portion of α-solanine is α-L-rhamnopyranosyl-(1→2gal)-O-β-D-glucopyranosyl-(1→3gal)-β-D-galactopyranose (or 6-deoxy-α-L-mannopyranosyl-(1→2)-O-[β-D-glucopyraonosyl-( 1→13)]β-D-galactopyranoside), whilst the triglycoside portion of α-chaconine is α-L-rhamnopyranosyl-(1→2glu)-O-α-L-rhamnopyranosyl-(1→4glu)-β-D-glucopyranose.

Some plant extracts containing mixtures of triglycoalkaloids differing only by the triglycoside portion described above, such as plant extracts containing solasonine and solamargine, have been shown to exhibit anticancer activity. To enable thorough investigation of the activity of such compounds and to enable the manufacture of pharmaceutical products containing one of such compounds or both of such compounds in a fixed ratio, it is highly desirable to obtain the compounds in substantially pure form. However, existing methods for separation of triglycoalkaloids having an identical alkaloid portion, such as solasonine and solamargine, are time consuming and difficult to effect on any reasonable scale, meaning 'pure' compounds are extremely expensive.

It is one object of the present invention to provide a relatively simple method for separation of triglycoalkaloids in which the triglycoside portion comprises α-L-rhamnopyranosyl-( 1→2gal)-O-β-D-glucopyranosyl-(1→3gal)-β-D-galactopyranose (or 6-deoxy-α-L-mannopyranosyl-(1→2)-O-[β-D-glucopyraonosyl-(1→3)]-β-D-galactopyranoside) from triglycoalkaloids in which the triglycoside portion is α-L-rhamnopyranosyl-( 1→2glu)-O-α-L-rhamnopyranosyl-(1→4glu)-β-D-glucopyranose from a mixture containing both compounds.

Throughout this specification, unless the context requires otherwise, the word 'separation' when used in relation to a mixture containing both triglycoalkaloids in which the triglycoside portion comprises α-L-rhamnopyranosyl-(1→2gal)-O-β-D-glucopyranosyl-( 1→3gal)-β-D-galactopyranose (or 6-deoxy-α-L-mannopyranosyl-( 1→2)-O-[β-D-glucopyraonosyl-(1→3)]-β-D-galactopyranoside) and triglycoalkaloids in which the triglycoside portion is α-L-rhamnopyranosyl-( 1→2glu)-O-α-L-rhamnopyranosyl-(1→4glu)-β-D-glucopyranose encompasses the enrichment of the mixture in either compound.

The preceding discussion of the background to the invention is intended to facilitate an understanding of the present invention. However, it should be appreciated that the discussion is not an acknowledgement or admission that any of the material referred to was part of the common general knowledge in Australia as at the priority date of the application.

Throughout the specification, unless the context requires otherwise, the word "comprise" or variations such as "comprises" or "comprising", will be understood to imply the inclusion of a stated integer or group of integers but not the exclusion of any other integer or group of integers.

Throughout this specification, unless the context specifies otherwise, reference to solamargine includes both the free base and solamargine salts, and reference to solasonine includes both the free base and solasonine salts.

Throughout this specification, unless the context requires otherwise, a triglycoalkaloid having a triglycoside portion comprising α-L-rhamnopyranosyl-( 1→2gal)-O-β-D-glucopyranosyl-(1→3gal)-β-D-galactopyranose (or 6-deoxy-α-L-mannopyranosyl-( 1→2)-O-[β-D-glucopyraonosyl-(1→3)]-β-D-galactopyranoside), such as solasonine, will be referred to as a 'rhamnose-glucose-galactose triglycoalkaloid', whilst a triglycoalkaloid having a triglycoside portion comprising α-L-rhamnopyranosyl-(1→2glu)-O-α-L-rhamnopyranosyl-(1→4glu)-β-D-glucopyranose, such as solamargine, will be referred to as a 'rhamnose-rhamnose-glucose triglycoalkaloid'.

DISCLOSURE OF THE INVENTION

In accordance with the present invention there is provided a method for the separation of a rhamnose-glucose-galactose triglycoalkaloid and a rhamnose-rhamnose-glucose triglycoalkaloid from a mixture containing both a rhamnose-glucose-galactose triglycoalkaloid and a rhamnose-rhamnose-glucose triglycoalkaloid, the method comprising the steps of:

Combining the mixture with a portion of alcoholic solvent;

Causing or allowing a substantial portion of the rhamnose-rhamnose-glucose triglycoalkaloid to dissolve, thereby generating an alcoholic solution substantially of the rhamnose-rhamnose-glucose triglycoalkaloid, and a solid substantially comprising the rhamnose-glucose-galactose triglycoalkaloid; and Separating the solid substantially comprising the rhamnose-glucose-galactose triglycoalkaloid from the solution substantially of the rhamnose-rhamnose-glucose triglycoalkaloid.

Preferably, the method comprises the further step of stripping the alcoholic solvent from the solution substantially of the rhamnose-rhamnose-glucose triglycoalkaloid to obtain a solid substantially comprising the rhamnose-rhamnose-glucose triglycoalkaloid.

In a preferred form of the invention, the alcoholic solvent comprises a low molecular weight alcohol. In a highly preferred form of the invention, the alcoholic solvent comprises methanol or ethanol.

If the rhamnose-glucose-galactose triglycoalkaloid and/or the rhamnose-rhamnose-glucose triglycoalkaloid are to be used for therapeutic purposes, then ethanol has the advantage of being non-toxic if left in residual amounts.

Preferably, the step of combining the mixture with a portion of alcohol solvent more specifically comprises:

Adding the mixture to the alcoholic solvent.

As the mixture is added to the alcoholic solvent, the combination of the alcoholic solvent and the mixture may be vigorously agitated.

After the step of causing or allowing a substantial portion of the rhamnose-rhamnose-glucose triglycoalkaloid to dissolve, thereby generating an alcoholic solution substantially of the rhamnose-rhamnose-glucose triglycoalkaloid, and a solid substantially comprising the rhamnose-glucose-galactose triglycoalkaloid, the method of the present invention preferably comprises the further step of:

Adding a portion of a further solvent to cause precipitation of at least a portion of any dissolved the rhamnose-glucose-galactose triglycoalkaloid.

In a specific form of the invention, the further solvent is ethyl acetate (ethyl ethanoate). Where the alcoholic solvent is methanol or ethanol, and the further solvent is ethyl ethanoate, the portion of further solvent corresponds to approximately 3 to 5 times the volume of alcoholic solvent. In a highly preferred form of the invention, the portion of further solvent corresponds to approximately 4 times the volume of alcoholic solvent.

In less preferred forms of the invention, the further solvent may be selected from alcohol miscible solvents including: acetone; acetonitrile, methyl ethyl ketone and methyl isobutyl ketone.

Where the alcoholic solvent is provided in the form of methanol or ethanol, the step of combining the mixture with a portion of alcohol solvent more specifically comprises the step of:

Combining the mixture with a portion of methanol or ethanol in a ratio of approximately 10L of methanol per kilogram of mixture.

The step of separating the solid substantially comprising the rhamnose-glucose-galactose triglycoalkaloid from the solution substantially of the rhamnose-rhamnose-glucose triglycoalkaloid, may more specifically comprise physically separating the solid substantially comprising the rhamnose-glucose-galactose triglycoalkaloid from the solution substantially of the rhamnose-rhamnose-glucose triglycoalkaloid, such as by filtration and/or centrifugation.

After the step of separating the solid substantially comprising the rhamnose-glucose-galactose triglycoalkaloid from the solution, the method of the present invention may further comprise the step of:

Purifying the solid substantially comprising the rhamnose-glucose-galactose triglycoalkaloid by recrystallisation.

Where the method comprises the step of stripping the alcoholic solvent from the solution comprised substantially of the rhamnose-rhamnose-glucose triglycoalkaloid to obtain a solid substantially comprising the rhamnose-rhamnose-glucose triglycoalkaloid, the method of the present invention may further comprise the step of:

Purifying the solid substantially comprising the rhamnose-rhamnose-glucose triglycoalkaloid by recrystallisation.

The steps of purifying the solid substantially comprising the rhamnose-rhamnose-glucose triglycoalkaloid and/or the solid substantially comprising the rhamnose-glucose-galactose triglycoalkaloid by recrystallisation may more specifically comprise the step of purifying the solid substantially comprising the rhamnose-rhamnose-glucose triglycoalkaloid and/or the solid substantially comprising the rhamnose-glucose-galactose triglycoalkaloid by recrystallisation in aqueous alcohol solutions. More specifically still, the step involves recrystallisation in aqueous solutions of low molecular weight alcohols. In a highly specific form of the invention, the step involves recrystallisation in aqueous solutions of methanol, ethanol or isopropanol, or mixtures of such.

Where the step involves recrystallisation in aqueous alcohol solutions, it is highly preferred that the aqueous alcohol solution comprises at least 10–15% alcohol.

In a specific form of the invention, the aqueous alcohol solution is provided in the form of an aqueous methanol solution with a methanol concentration between about 40 and 80%. More specifically, the methanol concentration is between about 50 and 70%.

In a specific form of the invention, the aqueous alcohol solution is provided in the form of an aqueous isopropyl alcohol solution with an isopropyl alcohol concentration of between about 20 and 50% isopropyl alcohol. More specifically, the isopropyl alcohol concentration is between about 25 and 40%.

The steps of purifying the solid substantially comprising the rhamnose-rhamnose-glucose triglycoalkaloid and/or the solid substantially comprising the rhamnose-glucose-galactose triglycoalkaloid by recrystallisation may involve multiple dissolution and crystallisation steps. In a specific form of the invention, the mixture of the rhamnose-glucose-galactose triglycoalkaloid and the rhamnose-rhamnose-glucose triglycoalkaloid is provided in the form of a plant extract.

Said plant extract may be produced by a method comprising the following steps:

Homogenising a portion of plant material containing a rhamnose-glucose-galactose triglycoalkaloid and a rhamnose-rhamnose-glucose triglycoalkaloid;

Adding an antioxidant to the homogenised plant material;

Separating solid material from the homogenised plant material to produce a first solution containing both the rhamnose-glucose-galactose triglycoalkaloid and the rhamnose-rhamnose-glucose triglycoalkaloid;

Inducing the precipitation of a first solid mixture of the rhamnose-glucose-galactose triglycoalkaloid and the rhamnose-rhamnose-glucose triglycoalkaloid; and Collecting the first solid mixture of the rhamnose-glucose-galactose triglycoalkaloid and the rhamnose-rhamnose-glucose triglycoalkaloid.

The mixture of the rhamnose-glucose-galactose triglycoalkaloid and the rhamnose-rhamnose-glucose triglycoalkaloid may be produced by a method comprising the following steps:

Homogenising a portion of plant material containing the rhamnose-glucose-galactose triglycoalkaloid and the rhamnose-rhamnose-glucose triglycoalkaloid;

Adding a quantity of pectinase to the homogenised plant material;

Separating solid material from the homogenised plant material to produce a first solution containing the rhamnose-glucose-galactose triglycoalkaloid and the rhamnose-rhamnose-glucose triglycoalkaloid;

Inducing the precipitation of a first solid mixture of the rhamnose-glucose-galactose triglycoalkaloid and the rhamnose-rhamnose-glucose triglycoalkaloid; and Collecting the first solid mixture of the rhamnose-glucose-galactose triglycoalkaloid and the rhamnose-rhamnose-glucose triglycoalkaloid;

The mixture of the rhamnose-glucose-galactose triglycoalkaloid and the rhamnose-rhamnose-glucose triglycoalkaloid may be produced by a method comprising the following steps:

Homogenising a portion of plant material containing the rhamnose-glucose-galactose triglycoalkaloid and the rhamnose-rhamnose-glucose triglycoalkaloid;

Placing the homogenised plant material in an inert atmosphere;

Separating solid material from the homogenised plant material to produce a first solution containing the rhamnose-glucose-galactose triglycoalkaloid and the rhamnose-rhamnose-glucose triglycoalkaloid;

Inducing the precipitation of a first solid mixture of the rhamnose-glucose-galactose triglycoalkaloid and the rhamnose-rhamnose-glucose triglycoalkaloid; and Collecting the first solid mixture of the rhamnose-glucose-galactose triglycoalkaloid and the rhamnose-rhamnose-glucose triglycoalkaloid.

In a preferred form of the invention, the method comprises the steps of

Homogenising a portion of plant material containing the rhamnose-glucose-galactose triglycoalkaloid and the rhamnose-rhamnose-glucose triglycoalkaloid;

Adding a quantity of pectinase to the homogenised plant material;

Adding an antioxidant to the homogenised plant material the rhamnose-glucose-galactose triglycoalkaloid and the rhamnose-rhamnose-glucose triglycoalkaloid;

Placing the homogenised plant material in an inert atmosphere;

Separating solid material from the homogenised plant material to produce a first solution containing the rhamnose-glucose-galactose triglycoalkaloid and the rhamnose-rhamnose-glucose triglycoalkaloid;

Inducing the precipitation of a first solid mixture of the rhamnose-glucose-galactose triglycoalkaloid and the rhamnose-rhamnose-glucose triglycoalkaloid; and Collecting the first solid mixture of the rhamnose-glucose-galactose triglycoalkaloid and the rhamnose-rhamnose-glucose triglycoalkaloid.

In accordance with the present invention, there is provided a method for the production of a mixture of the rhamnose-glucose-galactose triglycoalkaloid and the rhamnose-rhamnose-glucose triglycoalkaloid as described above.

The method may comprise the additional step of:

Adding a quantity of acid solution to the homogenised plant material to reduce the pH to approximately 4 or below.

In one form of the invention, the acid solution is provided in the form of an acetic acid solution.

In one form of the invention, after the step of separating the solid material from the, homogenised plant material to produce a first solution containing the rhamnose-glucose-galactose triglycoalkaloid and the rhamnose-rhamnose-glucose triglycoalkaloid, the method may comprise the additional step of:

Washing the solid material with a portion of acid solution and adding the washings to the first solution containing the rhamnose-glucose-galactose triglycoalkaloid and the rhamnose-rhamnose-glucose triglycoalkaloid.

The method may comprise the additional steps of:

Dissolving the first solid mixture of the rhamnose-glucose-galactose triglycoalkaloid and the rhamnose-rhamnose-glucose triglycoalkaloid in a further quantity of acid to produce a second solution containing the rhamnose-glucose-galactose triglycoalkaloid and the rhamnose-rhamnose-glucose triglycoalkaloid;

Separating the second solution containing the rhamnose-glucose-galactose triglycoalkaloid and the rhamnose-rhamnose-glucose triglycoalkaloid from any residual solids;

Inducing the precipitation of a second solid mixture of the rhamnose-glucose-galactose triglycoalkaloid and the rhamnose-rhamnose-glucose triglycoalkaloid; and Collecting the second solid mixture of the rhamnose-glucose-galactose triglycoalkaloid and the rhamnose-rhamnose-glucose triglycoalkaloid.

The second solid mixture of solasonine and solamargine may be washed with water.

In one form of the invention, after the second mixture of the rhamnose-glucose-galactose triglycoalkaloid and the rhamnose-rhamnose-glucose triglycoalkaloid is optionally washed with water, the mixture of the rhamnose-glucose-galactose triglycoalkaloid and the rhamnose-rhamnose-glucose triglycoalkaloid is dissolved in boiling ethanol to produce a third solution of the rhamnose-glucose-galactose triglycoalkaloid and the rhamnose-rhamnose-glucose triglycoalkaloid, the third solution being filtered when hot, before a volume of water is added, thereby inducing precipitation of a third solid mixture of the rhamnose-glucose-galactose triglycoalkaloid and the rhamnose-rhamnose-glucose triglycoalkaloid. Preferably, the volume of water added corresponds to approximately 6 times the volume of the ethanolic solution of the rhamnose-glucose-galactose triglycoalkaloid and the rhamnose-rhamnose-glucose triglycoalkaloid.

This technique has the advantage of minimising the presence of water-soluble glycoalkaloids in the solid mixture of solasonine and solamargine.

The third solid mixture of the rhamnose-glucose-galactose triglycoalkaloid and the rhamnose-rhamnose-glucose triglycoalkaloid may then be collected by centrifugation.

In one form of the invention, the antioxidant is provided in the form of sodium metabisulphite. Where the antioxidant is provided in the form of sodium metabisulphite, the metabisulphite is preferably added to a concentration of approximately 0.5% by weight of the fresh plant material.

In one form of the invention, the inert atmosphere is provided by way of a nitrogen atmosphere.

Before the step(s) of inducing the precipitation of the first solid mixture of the rhamnose-glucose-galactose triglycoalkaloid and the rhamnose-rhamnose-glucose triglycoalkaloid, the method may involve the step of heating the solution of the rhamnose-glucose-galactose triglycoalkaloid and the rhamnose-rhamnose-glucose triglycoalkaloid. In a specific form of the invention, the step comprises heating the solution to about 40–60° C. In a highly specific form of the invention, the step involves heating the solution to approximately 50° C.

The step(s) of inducing the precipitation of the first solid mixture of the rhamnose-glucose-galactose triglycoalkaloid and the rhamnose-rhamnose-glucose triglycoalkaloid may comprise the step of adding sufficient ammonium hydroxide to raise the pH of the solution to the point where the rhamnose-glucose-galactose triglycoalkaloid and the rhamnose-rhamnose-glucose triglycoalkaloid precipitate as a mixture of the free bases.

Alternately, step of inducing the precipitation of the first solid mixture of the rhamnose-glucose-galactose triglycoalkaloid and the rhamnose-rhamnose-glucose triglycoalkaloid may comprise the addition of an ammonium salt of an acid, whereupon the rhamnose-glucose-galactose triglycoalkaloid and the rhamnose-rhamnose-glucose triglycoalkaloid precipitate as a mixture of the salts of the acid.

In one form of the invention, the acid is phenylacetic acid.

In accordance with the present method, there is further provided a pharmaceutical composition comprising an aqueous solution of a phenylacetate salt of the rhamnose-glucose-galactose triglycoalkaloid and/or the rhamnose-rhamnose-glucose triglycoalkaloid.

Where the rhamnose-glucose-galactose triglycoalkaloid and the rhamnose-rhamnose-glucose triglycoalkaloid are solasonine and solamargine respectively, the mixture of solasonine and solamargine is provided in the form of an extract from a plant of the genus Solanum. In a highly specific form of the invention, the mixture of solasonine and solamargine is provided in the form of an extract from a plant of the species *Solanum linnaeanum*. When the mixture of solasonine and solamargine is provided in the form of an extract from a plant of the species *Solanum linnaeanum*, the extract is preferably from the fruit of the plant. Preferably still, the extract is from the green fruit of the plant.

In one form of the invention, the rhamnose-glucose-galactose triglycoalkaloid is provided in the form of solasonine and the rhamnose-rhamnose-glucose triglycoalkaloid in the form of solamargine.

Where the rhamnose-glucose-galactose triglycoalkaloid is provided in the form of solasonine and the rhamnose-rhamnose-glucose triglycoalkaloid in the form of solamargine, the solid substantially comprising the rhamnose-glucose-galactose triglycoalkaloid in the form of solasonine preferably comprises at least 80% by weight solasonine. Preferably still, the solid substantially comprising solasonine comprises at least 90% by weight solasonine. Further and still preferably, the solid substantially comprising solasonine comprises approximately 94% by weight solasonine.

Where the rhamnose-glucose-galactose triglycoalkaloid is provided in the form of solasonine and the rhamnose-rhamnose-glucose triglycoalkaloid in the form of solamargine, the solid substantially comprising the rhamnose-rhamnose-glucose triglycoalkaloid in the form of solamargine preferably comprises at least 80% by weight solamargine. Preferably still, the solid substantially comprising solamargine comprises at least 90% by weight solamargine. Further and still preferably, the solid substantially comprising solamargine comprises approximately 97% by weight solamargine.

Where the rhamnose-glucose-galactose triglycoalkaloid is provided in the form of solasonine and the rhamnose-rhamnose-glucose triglycoalkaloid in the form of solamargine, in a specific form of the invention, the step of causing or allowing a substantial portion of the rhamnose-rhamnose-glucose triglycoalkaloid in the from of solamargine to dissolve, thereby generating an alcoholic solution substantially of solamargine, and a solid substantially comprising the rhamnose-glucose-galactose triglycoalkaloid in the form of solasonine more specifically comprises:

Causing or allowing a substantial portion of the solamargine to dissolve over a period of approximately 1 to 3 hours at room temperature, thereby generating an alcoholic solution substantially of solamargine, and a solid substantially comprising solasonine.

In accordance with the present method, there is further provided a pharmaceutical composition comprising an aqueous solution of a phenylacetate salt of the solasonine and/or solamargine.

BEST MODE(S) FOR CARRYING OUT THE INVENTION

The best method for performing the invention will now be described. The best method is described by way of example only, and should not be construed as in any way limiting the foregoing description of the invention.

A portion of green fruit from a plant or plants of the species *Solanum linnaeanum* is minced and passed through a 5 mm sieve. The sieved mixture is then placed in an inert atmosphere, whereupon a portion of antioxidant in the form of sodium metabisulphite, corresponding to approximately 0.5% of the mass of the fresh fruit, is added to such, as is an amount of pectinase, corresponding to approximately 1 mg per kg of fruit.

The mixture is then physically separated by pressure filtration and/or centrifugation to separate the solids from the solution containing both solasonine and solamargine. The solids are then washed with a volume of 3% acetic acid corresponding to the volume of solution obtained from the pulp mixture, and the washings combined with the supernatant from the centrifugation.

After the solution is heated to approximately 50° C., precipitation of a mixture of the free bases solamargine and solasonine is induced by the addition of a portion of ammonium hydroxide.

The solid mixture of free bases of solasonine and solamargine are collected by centrifugation, with the supernatant being discarded. The solid mixture so produced is then dissolved in a 3% solution of acetic acid, with the resulting solution being separated from any residual solids by filtration. After the solution is heated to approximately 50° C., a further portion of ammonium hydroxide is added, inducing the precipitation of a solid mixture of the free bases, which are then washed in water, before being dissolved in boiling ethanol and filtered. An amount of water equivalent to six times the volume of the ethanolic solution is then added, thereby inducing the precipitation of a solid mixture of solasonine and solamargine at a ratio of between about 40:60 and 60:40. The solid is then collected by centrifugation. The mixture is typically 80–100% pure, with mono- and diglycoalkaloids and other water soluble impurities being largely removed.

A desired quantity of the mixture of solasonine and solamargine is weighed and introduced into a suitable vessel. A volume of methanol, corresponding to 10 mL per gram of the mixture is slowly added, portion wise, over a period of 10–15 minutes with vigorous stirring/agitation. As dissolution occurs the colour of the solution should darken to light brown-tan with simultaneous appearance of a fine white precipitate. As stirring commences the undissolved lumps of solid mixture should gradually break up, and the process may be accelerated using a sonic bath and breaking up lumps with a spatula/stirring rod.

After a period of 1–3 hours, depending on the presence of undissolved lumps/residue, a milky white suspension/slurry is obtained. Whilst this solid may be collected, a better yield, albeit at lower purity, is obtained by adding (in one addition) 4 equivalents of ethyl acetate i.e. 4× volume of methanol employed, resulting in the immediate precipitation of a white suspension. The white suspension may then be filtered by Buchner vacuum filtration (using Whatman #1 filter paper), with any material remaining in the flask being washed out with small amounts of ethyl acetate. The resulting white solid should then be left to dry on the filter (under vacuum) until touch dry, producing a solid substantially comprising solasonine. After drying in a vacuum oven at 60° C. for a period of 2–3 hours, analysis should show that the solid comprises approximately 85% solasonine, with the recovery of material being approximately 90–100%.

The filtrate solution (supernatant) remaining in the Buchner flask may then be transferred to a round bottom flask (washing with methanol) and the solvent removed to leave a white solid. The white solid obtained may be further dried using a vacuum oven (see above). On analysis the solid should contain approximately 97% solamargine, with the recovery of material being approximately 90–100%.

The solid solasonine and solamargine are then further purified by recrystallisation in an aqueous solution of isopropanol, ethanol or methanol, with the precise conditions representing a trade-off between speed of recrystallisation and % recovery vs purity of recovered solid.

EXAMPLES

Certain aspects of the present invention are exemplified by way of the following examples. The examples should not be construed as in any way limiting the preceding broad description of the invention.

1. Isolation of Mixture of Solasonine and Solamargine from Plant Material

A portion of green fruit from a plant or plants of the species *Solanum linnaeanum* was minced and passed through a 5 mm sieve. The sieved mixture was then placed in an inert atmosphere, whereupon a portion of 3% acetic acid (corresponding to 1 litre per 500 g of plant material) and a portion of antioxidant in the form of sodium metabisulphite, corresponding to approximately 0.5% of the mass of the fresh fruit, is added to such, as is an amount of pectinase, corresponding to 1 mg per kg of fruit.

The mixture was then filtered and centrifuged to separate the solids from a solution containing both solasonine and solamargine. After the solution was heated to approximately 50° C., precipitation of a mixture of the free bases of solamargine and solasonine was induced by the addition of a portion of ammonium hydroxide.

The solid mixture of the free bases of solasonine and solamargine were collected by centrifugation, with the supernatant being discarded. The solid mixture so produced was then dissolved in a 3% solution of acetic acid, with the resulting solution being separated from any residual solids by filtration. After the solution was heated to approximately 50° C., a further portion of ammonium hydroxide was added, inducing the precipitation of a solid mixture of the free bases of solasonine and solamargine, which was then washed in water, before being dissolved in boiling ethanol and filtered. The equivalent of six volumes of water were added to the filtrate to induce precipitation of a solid mixture of solasonine and solamargine at a ratio of about 50:50, and with a purity of 98–99%, which was collected by centrifugation.

2. Production of Solasonine and Solamargine Salts

Precipitation of Tosyl Salts

One gram of the solid mixture of solasonine and solamargine, produced as described above was dissolved in 10 mL of 3% acetic acid. A 4 mL portion of 0.5M ammonium hydroxide, containing 1.5 equivalents of p-toluene sulfonic acid was added to the solution, resulting in the precipitation of a mixture of the tosyl salts of solasonine and solamargine.

Precipitation of Phenylacetate Salts

A mixture of solasonine and solamargine (in an approximately 1:1 ratio) (1.0 g) was dissolved in 10 mL of 3% acetic acid. Phenylacetic acid (0.255 g) was dissolved in 0.5M ammonium hydroxide (3.75 mL) and added dropwise to the solution. The mixture was left at 4° C. overnight to give a settled fine white powder. The suspension was centrifuged to give a solid and supernatant. On analysis the solid composition contained solasonine:solamargine salts in the ratio 63:37. The supernatant composition of solasonine:solamargine was 34:66.

Several other salts were produced by analogous methods, and it was noted that the salt of phenylacetic acid exhibited superior handling properties. Specifically, the phenyl acetate salt was found to be soluble in water at physiological pH ranges.

3. Separation of Solasonine and Solamargine

Methanol—Ethyl Acetate

A desired quantity of a mixture of solasonine and solamargine was weighed and added portion-wise to a stirred methanol solution, corresponding in volume to 10 mL per gram of the mixture, over a period of 10–15 minutes. As dissolution occurred the colour of the solution darkened to light brown-tan with simultaneous appearance of a fine white precipitate. As stirring commenced the undissolved lumps of solid mixture gradually broke up.

After a brief period a milky white suspension/slurry was obtained. HPLC analysis of the solid present at this stage showed 94% solasonine. Four equivalents of ethyl acetate were added (in one addition), resulting in the immediate precipitation of a white suspension. The white suspension was then filtered by Buchner vacuum filtration (using Whatman #1 filter paper), with any material remaining in the flask being washed out with small amounts of ethyl acetate. The resulting white solid was left to dry on the filter (under vacuum) until touch dry and the solid obtained has a powdery consistency. The white solid was dried in a vacuum oven at 60° C. for a period of 2–3 hrs, analysis of the solid showing approx. 85% solasonine (% recovery of material ~90–100%).

The filtrate solution (supernatant) remaining in the Buchner flask was transferred to a round bottom flask (washing with methanol) and the solvent stripped by rotary vacuum evaporation (bath temp. 60° C.), leaving a white solid. The white solid obtained can be further dried using a vacuum oven (see above). On HPLC analysis the solid contained approx. 97% solamargine (% recovery of material ~90–100%).

Methanol

To 1 g of a mixture of solasonine and solamargine, wherein the ratio of solasonine to solamargine was approximately 1:1, methanol (20 mL) was added with stirring for 1 hour. The sample dissolved while concurrently, a fine white precipitate formed. The suspension was left stirring for several hours without any noticeable change in the suspension. The suspension was vacuum filtered and the white powder analysed. The powder contained solasonine:solamargine in the ratio 96:4. The supernatant contained solasonine:solamargine in the ratio 30:70.

Methanol—Acetonitrile

A 2 g portion of a mixture of solasonine and solamargine, wherein the ratio of solasonine to solamargine was approximately 1:1, was dissolved in methanol (75 mL). During the dissolution it was noted that initial solution was concurrently replaced by a fine white precipitate. Acetonitrile (250 mL) was added yielding a white precipitate. The suspension was vacuum filtered and the precipitate and filtrate analysed. For the precipitate, composition was solasonine:solamargine 74:26 and for the filtrate 30:70

Methanol—Ethylacetate

A number of experiments were conducted using methanol and ethyl acetate as described above, however, the amount of ethyl acetate added to was varied, as set out in the table below, showing that the best results were obtained at a 1:4 ratio.

TABLE 1

Effect of different ratios of methanol/ethyl acetate on solasonine/solamargine separation

| MeOH/EtOAc Ratio | % SS Purity (precipitate) | % SS Recovery | % SM Purity (supernatant) |
|---|---|---|---|
| 1:1 | 89 | 40 | 66 |
| 1:2 | 95 | 62 | 79 |
| 1:3 | 95 | 74 | 87 |
| 1:4 | 95 | 86 | 92* |
| 1:5 | 94 | 85 | 95* |
| 1:10 | 93 | 90 | 96* |

*=Values following vacuum rotary evaporation of supernatant.

Similar experiments were undertaken using ethanol as the alcoholic solvent. Although a gel was produced rather than the solid obtained from methanol, it is envisaged that the fact that ethanol residues are more pharmaceutically acceptable that methanol residues makes the use of ethanol preferable in some situations.

4. Recrystallisation

A series of recrystallisation experiments were undertaken, employing a range of aqueous alcoholic solvents. The basic method employed was as follows:

The minimum amount of alcoholic solvent was employed, and the mixture heated in a hot sand bath or water bath to dissolve the solid material. Additional solvent was added if the solid failed to dissolve adequately within a period of 10–15 minutes. If a trace amount of undissolved material was present then hot filtration through a hot funnel was undertaken. In all instances slow cooling of the solution (e.g. on a cork ring) was employed. On reaching room temperature deposition of recrystallised material was observed. Depending on the initial % purity of material, solasonine appears as fine white needles and solamargine as a white amorphous solid. Further cooling on ice or overnight refrigeration usually generates more solid material.

The results of the experiments appear in Tables 2 to 5, below, where MeOH is used to denote methanol and IPA isopropyl alcohol. The results demonstrate that % Purity and recovery of material varies according to amount of alcohol and initial % purity of the solid from the purification process. Further, The number of recrystallisation steps required for each solid varies from 1–3 steps and is dependent on the initial % purity of material. As a general rule, if the solasonine content is 90–94%, recrystallisation to 98–99% purity can be achieved in 1–2 steps (1 step for 94% or above)—see Table 2 for 1 step results. For material of 80–90% solasonine, purification of 98–99% requires 2–3 steps—see Table 3 for 1 step results. Recrystallisation of 90–95% solamargine to 98–99% purity is achievable in 2–3 steps (usually 3) e.g. 1 step from 89.5% solamargine generates 93.1% solamargine material with 52% recovery. If solamargine % purity is 96–97% (or above) purification to 98–99% solamargine can be achieved in 1–2 recrystallisation steps—see Table 4 and 5.

The experiments also demonstrated that if the alcohol content of the solvent mixture exceeds 80% recrystallisation is usually very slow (1–2 weeks) with poor recovery (20–30%). However, % purity is generally high even after 1 step (98–99%). Further, it was discovered that if alcohol content drops below 10–15%, recrystallisation is not possible due to aqueous insolubility of the solid (even when hot).

TABLE 2

1 Step Recrystallisation of 83.4% Solasonine (SS)

| Aqueous Recrystallisation Solvent | % SS Purity | % SS Recovery |
|---|---|---|
| 55% MeOH | 93.1 | 61 |
| 60% MeOH | 95.8 | 38 |
| 70% MeOH | 95.8 | 9 |
| 35% IPA | 92.6 | 71 |
| 40% IPA | 94.1 | 29 |

TABLE 3

1 Step Recrystallisation of 92.0% Solasonine (SS)

| Aqueous Recrystallisation Solvent | % SS Purity | % SS Recovery |
|---|---|---|
| 50% MeOH | 95.3 | 79 |
| 55% MeOH | 94.6# | 79 |
| 40% IPA | 96.7 | 85 |

Additional results were as follows:
From 93.2% SS, using 35% IPA: 97.6% purity, 80% recovery.
From 93.3% SS, using 50% MeOH: 99.0% purity, 68% recovery.

TABLE 4

1 Step Recrystallisation of 95.9% Solamargine (SM)

| Aqueous Recrystallisation Solvent | % SM Purity | % SM Recovery |
|---|---|---|
| 50% MeOH | 98.5 | 57 |
| 55% MeOH | 97.0 | 62 |

TABLE 4-continued

1 Step Recrystallisation of 95.9% Solamargine (SM)

| Aqueous Recrystallisation Solvent | % SM Purity | % SM Recovery |
|---|---|---|
| 60% MeOH | 96.7 | 31 |
| 25% IPA | 96.6 | 76 |
| 30% IPA | 97.0 | 72 |
| 35% IPA | 97.4 | 57 |

TABLE 5

1 Step Recrystallisation of 96.8% Solamargine (SM)

| Aqueous Recrystallisation Solvent | % SM Purity | % SM Recovery |
|---|---|---|
| 55% MeOH | 98.5 | 54 |
| 60% MeOH | 98.7 | 46 |
| 65% MeOH | 98.5 | 63 |
| 30% IPA | 97.4 | 86 |
| 35% IPA | 97.8 | 72 |
| 40% IPA | 98.4 | 66 |

As the preceding examples demonstrate, the present invention demonstrates an effective and straightforward method for the separation of solasonine and solamargine from a mixture containing both compounds.

Modifications and variations such as would be apparent to the skilled addressee are considered to fall within the scope of this invention.

What is claimed is:

1. A method for the separation of a rhamnose-glucose-galactose triglycoalkaloid and a rhamnose-rhamnose-glucose triglycoalkaloid from a mixture containing both the rhamnose-glucose-galactose triglycoalkaloid and the rhamnose-rhamnose-glucose triglycoalkaloid, the method comprising the steps of:
    Combining the mixture with a portion of alcoholic solvent;
    Causing or allowing a substantial portion of the rhamnose-rhamnose-glucose triglycoalkaloid to dissolve, thereby generating an alcoholic solution substantially of the rhamnose-rhamnose-glucose triglycoalkaloid, and a solid substantially comprising the rhamnose-glucose-galactose triglycoalkaloid; and
    Separating the solid substantially comprising the rhamnose-glucose-galactose triglycoalkaloid from the solution substantially of the rhamnose-rhamnose-glucose triglycoalkaloid.

2. A method according to claim 1 characterised in that the method further comprises the step of:
    Stripping the alcoholic solvent from the solution substantially of the rhamnose-rhamnose-glucose triglycoalkaloid to obtain a solid substantially comprising the rhamnose-rhamnose-glucose triglycoalkaloid.

3. A method according to claim 2 characterised in that, after the step of stripping the alcoholic solvent from the solution comprised substantially of the rhamnose-rhamnose-glucose triglycoalkaloid to obtain a solid substantially comprising the rhamnose-rhamnose-glucose triglycoalkaloid, the method of the present invention may further comprise the step of:
    Purifying the solid substantially comprising the rhamnose-rhamnose-glucose triglycoalkaloid by recrystallisation.

4. A method according to claim 2 characterised in that the step of purifying the solid substantially comprising the rhamnose-rhamnose-glucose triglycoalkaloid and/or the solid substantially comprising the rhamnose-glucose-galactose triglycoalkaloid by recrystallisation comprises:
    Purifying the solid substantially comprising the rhamnose-rhamnose-glucose triglycoalkaloid and/or the solid substantially comprising the rhamnose-glucose-galactose triglycoalkaloid by recrystallisation in aqueous alcohol solutions.

5. A method according to claim 2 characterised in that the step of purifying the solid substantially comprising the rhamnose-rhamnose-glucose triglycoalkaloid and/or the solid substantially comprising the rhamnose-glucose-galactose triglycoalkaloid by recrystallisation comprises:
    Purifying the solid substantially comprising the rhamnose-rhamnose-glucose triglycoalkaloid and/or the solid substantially comprising the rhamnose-glucose-galactose triglycoalkaloid by recrystallisation in aqueous solutions of low molecular weight alcohols.

6. A method according to claim 5 characterised in that in that the step of purifying the solid substantially comprising the rhamnose-rhamnose-glucose triglycoalkaloid and/or the solid substantially comprising the rhamnose-glucose-galactose triglycoalkaloid by recrystallisation comprises:
    Purifying the solid substantially comprising the rhamnose-rhamnose-glucose triglycoalkaloid and/or the solid substantially comprising the rhamnose-glucose-galactose triglycoalkaloid by recrystallisation in aqueous solutions of methanol, ethanol or isopropanol, or mixtures of such.

7. A method according to claim 2 characterised in that the step of purifying the solid substantially comprising the rhamnose-rhamnose-glucose triglycoalkaloid and/or the solid substantially comprising the rhamnose-glucose-galactose triglycoalkaloid by recrystallisation comprises:
    Purifying the solid substantially comprising the rhamnose-rhamnose-glucose triglycoalkaloid and/or the solid substantially comprising the rhamnose-glucose-galactose triglycoalkaloid by recrystallisation in an aqueous solution of a low molecular weight alcohol comprising at least 10–15% alcohol.

8. A method according to claim 2 characterised in that the step of purifying the solid substantially comprising the rhamnose-rhamnose-glucose triglycoalkaloid and/or the solid substantially comprising the rhamnose-glucose-galactose triglycoalkaloid by recrystallisation comprises:
    Purifying the solid substantially comprising the rhamnose-rhamnose-glucose triglycoalkaloid and/or the solid substantially comprising the rhamnose-glucose-galactose triglycoalkaloid by recrystallisation in an aqueous methanol solution with a methanol concentration between about 40 and 80%.

9. A method according to claim 2 characterised in that the step of purifying the solid substantially comprising the rhamnose-rhamnose-glucose triglycoalkaloid and/or the solid substantially comprising the rhamnose-glucose-galactose triglycoalkaloid by recrystallisation comprises:
    Purifying the solid substantially comprising the rhamnose-rhamnose-glucose triglycoalkaloid and/or the solid substantially comprising the rhamnose-glucose-galactose triglycoalkaloid by recrystallisation in an aqueous methanol solution with a methanol concentration between about 50 and 70%.

10. A method according to claim 2 characterised in that the step of purifying the solid substantially comprising the rhamnose-rhamnose-glucose triglycoalkaloid and/or the solid substantially comprising the rhamnose-glucose-galactose triglycoalkaloid by recrystallisation comprises:

Purifying the solid substantially comprising the rhamnose-rhamnose-glucose triglycoalkaloid and/or the solid substantially comprising the rhamnose-glucose-galactose triglycoalkaloid by recrystallisation in an aqueous isopropyl alcohol solution with an isopropyl alcohol concentration of between about 20 and 50% isopropyl alcohol.

11. A method according to claim 2 characterised in that the step of purifying the solid substantially comprising the rhamnose-rhamnose-glucose triglycoalkaloid and/or the solid substantially comprising the rhamnose-glucose-galactose triglycoalkaloid by recrystallisation comprises:

Purifying the solid substantially comprising the rhamnose-rhamnose-glucose triglycoalkaloid and/or the solid substantially comprising the rhamnose-glucose-galactose triglycoalkaloid by recrystallisation in an aqueous isopropyl alcohol solution with an isopropyl alcohol concentration of between about 25 and 40% isopropyl alcohol.

12. A method according to claim 1 characterised in that, the alcoholic solvent comprises a low molecular weight alcohol.

13. A method according to claim 12, charaterized in that the low molecular weight alcohol is isopropanol.

14. A method according to claim 1 characterised in that the alcoholic solvent is selected from the group consisting of methanol and ethanol.

15. A method according to claim 14 characterised in that the step of combining the mixture with a portion of alcohol solvent more specifically comprises the step of:

Combining the mixture with a portion of methanol or ethanol in a ratio of approximately 10 L of methanol or ethanol per kilogram of mixture.

16. A method according to claim 1 characterised in that the step of combining the mixture with a portion of alcohol solvent more specifically comprises:

Adding the mixture to the alcoholic solvent.

17. A method according to claim 1 characterised in that, after the step of causing or allowing a substantial portion of the rhamnose-rhamnose-glucose triglycoalkaloid to dissolve, thereby generating an alcoholic solution substantially of the rhamnose-rhamnose-glucose triglycoalkaloid, and a solid substantially comprising the rhamnose-glucose-galactose triglycoalkaloid, the method comprises the further step of:

Adding a portion of a further solvent to cause precipitation of at least a portion of any dissolved the rhamnose-glucose-galactose triglycoalkaloid.

18. A method according to claim 17 characterised in that the further solvent is ethyl acetate.

19. A method according to claim 17 characterised in that the alcoholic solvent is selected from the group consisting of methanol and ethanol; the further solvent is ethyl acetate and the portion of further solvent corresponds to approximately 3 to 5 times the volume of alcoholic solvent.

20. A method according to claim 17 characterised in that the alcoholic solvent is selected from the group consisting of methanol and ethanol; the further solvent is ethyl acetate and the portion of further solvent corresponds to approximately 4 times the volume of alcoholic solvent.

21. A method according to claim 1 characterised in that the step of separating the solid substantially comprising the rhamnose-glucose-galactose triglycoalkaloid from the solution substantially of the rhamnose-rhamnose-glucose triglycoalkaloid, more specifically comprises separating the solid substantially comprising the rhamnose-glucose-galactose triglycoalkaloid from the solution substantially of the rhamnose-rhamnose-glucose triglycoalkaloid by physical means such as by filtration and/or centrifugation.

22. A method according to claim 1 characterised in that, after the step of separating the solid substantially comprising the rhamnose-glucose-galactose triglycoalkaloid from the solution, the method of the present invention may further comprise the step of:

Purifying the solid substantially comprising the rhamnose-glucose-galactose triglycoalkaloid by recrystallisation.

23. A method according to claim 1 characterised in that the rhamnose-glucose-galactose triglycoalkaloid is solasonine and the rhamnose-rhamnose-glucose triglycoalkaloid is solamargine.

24. A method according to claim 23 characterised in that the solid substantially comprising the rhamnose-glucose-galactose triglycoalkaloid in the form of solasonine comprises at least 80% by weight solasonine.

25. A method according to claim 23 characterized in that the solid substantially comprising the rhamnose-glucose-galactose triglycoalkaloid in the form of solasonine comprises at least 90% by weight solasonine.

26. A method according to claim 23 characterised in that the solid substantially comprising the rhamnose-glucose-galactose triglycoalkaloid in the form of solasonine comprises approximately 94% by weight solasonine.

27. A method according to claim 23 characterised in that the solid substantially comprising the rhamnose-rhamnose-glucose triglycoalkaloid in the form of solamargine comprises at least 80% by weight solamargine.

28. A method according to claim 23 characterised in that the solid substantially comprising the rhamnose-rhamnose-glucose triglycoalkaloid in the form of solamargine comprises at least 90% by weight solamargine.

29. A method according to claim 23 characterised in that the solid substantially comprising the rhamnose-rhamnose-glucose triglycoalkaloid in the form of solamargine comprises approximately 97% by weight solamargine.

30. A method according to claim 23 characterised in that the step of causing or allowing a substantial portion of the rhamnose-rhamnose-glucose triglycoalkaloid in the from of solamargine to dissolve, thereby generating an alcoholic solution substantially of solamargine, and a solid substantially comprising the rhamnose-glucose-galactose triglycoalkaloid in the form of solasonine more specifically comprises:

Causing or allowing a substantial portion of the solamargine to dissolve over a period of approximately 1 to 3 hours at room temperature, thereby generating an alcoholic solution substantially of solamargine, and a solid substantially comprising solasonine.

* * * * *

UNITED STATES PATENT AND TRADEMARK OFFICE
CERTIFICATE OF CORRECTION

PATENT NO. : 6,984,725 B2  Page 1 of 1
APPLICATION NO. : 10/461737
DATED : January 10, 2006
INVENTOR(S) : Stephen Carter et al.

It is certified that error appears in the above-identified patent and that said Letters Patent is hereby corrected as shown below:

Column 14, line 24, replace "in that in that" with --in that--.
Column 16, line 51, replace "from" with --form--.

Signed and Sealed this

Fifth Day of December, 2006

JON W. DUDAS
*Director of the United States Patent and Trademark Office*